US010330655B2

(12) United States Patent
Du et al.

(10) Patent No.: US 10,330,655 B2
(45) Date of Patent: Jun. 25, 2019

(54) AIR QUALITY FORECASTING BASED ON DYNAMIC BLENDING

(71) Applicant: International Business Machines Corporation, Armonk, NY (US)

(72) Inventors: Hui Du, Beijing (CN); Yu Du, Beijing (CN); Si Huang, Beijing (CN); Yu Jia Tang, Beijing (CN); Bao Guo Xie, Beijing (CN); Meng Zhang, Beijing (CN); Xin Zhang, Lafayette, CO (US); Shuai Zhu, Beijing (CN)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 338 days.

(21) Appl. No.: 15/403,212

(22) Filed: Jan. 11, 2017

(65) Prior Publication Data
US 2018/0196023 A1 Jul. 12, 2018

(51) Int. Cl.
  *G01N 33/00* (2006.01)
  *G06F 19/00* (2018.01)
  *G01W 1/10* (2006.01)

(52) U.S. Cl.
  CPC .......... *G01N 33/0036* (2013.01); *G01W 1/10* (2013.01); *G06F 19/704* (2013.01)

(58) Field of Classification Search
  CPC .... G01N 33/0036; G01W 1/10; G06F 19/704
  See application file for complete search history.

(56) References Cited

U.S. PATENT DOCUMENTS

| 9,274,251 B2 | 3/2016 | Pasken et al. | |
| 2017/0184561 A1* | 6/2017 | Bai | ........... G01N 33/0062 |
| 2018/0239057 A1* | 8/2018 | Bai | ................ G01W 1/10 |

FOREIGN PATENT DOCUMENTS

| CN | 103163278 B | 4/2015 | |
| CN | 104881582 A | 9/2015 | |
| WO | WO-2016155372 A1 * | 10/2016 | ......... G06Q 10/04 |

OTHER PUBLICATIONS

Khalid J. Siddzqui et al., Knowledge Based System for Weather Information Processing and Forecasting, 1996, IEEE, pp. 1099-1101.*

(Continued)

*Primary Examiner* — Mischita L Henson
(74) *Attorney, Agent, or Firm* — Cantor Colburn LLP; Grant Johnson

(57) ABSTRACT

According to one or more embodiments of the present invention, a method of forecasting air quality is provided. The method includes determining weather pattern classifications based on global atmospheric information from a global weather model and determining a synoptic scale correction factor in response to the determination of the weather pattern classifications. The method also includes blending the global atmospheric information the synoptic scale correction factor to produce a data set and blending the data set with regional atmospheric information from a regional weather model to generate weather fields. The method further includes blending chemical information from a global chemical model and the synoptic scale correction factor to produce a second data set and blending the second data set into a regional chemical model based on the weather fields to forecast the air quality.

20 Claims, 5 Drawing Sheets

(56) References Cited

OTHER PUBLICATIONS

Lu Bai et al., Air Pollution Forecasts: An Overview, Apr. 1, 2018, International Journal of Environmental Research and Public Health, 15(4), 780.*
Sue Ellen Haupt et al., Big Data and Machine Learning for Applied Weather Forecasts, 2015, IEEE Symposium Series on Computational Intelligence, pp. 496-501.*
Kaixi Zhu, Stochastic Local-to-Global Methods for Air Quality Prediction, 2017, International Conference on Computational Science and Computational Intelligence, pp. 258-260.*
Xia Xi et al., A Comprehensive Evaluation of Air Pollution Prediction Improvement by a Machine Learning Method, 2015, IEEE International Conference on Service Operations and Logistics, and Informatics (SOLI), pp. 176-181.*
William F. Ryan, The air quality forecast rote: Recent changes and future challenges, 2016, Journal of the Air & Waste Management Association, vol. 66, No. 6, pp. 576-596.*

* cited by examiner

AIR QUALITY FORECASTING BASED ON DYNAMIC BLENDING

BACKGROUND

The present invention relates generally to forecasting air quality, and more specifically, to air quality forecasting based on dynamic blending of global and regional data with a synoptic scale correction factor.

In general, the accuracy of known air quality forecasting numerical models decreases with the model's integration time. The decrease in accuracy can result from a variety of sources. By way of example and without limitation, large scale information cannot be captured well with known models.

SUMMARY

According to one or more embodiments of the present invention, a method of forecasting air quality. Such embodiments include determining weather pattern classifications based on global atmospheric information from a global weather model and determining a synoptic scale correction factor in response to the determination of the weather pattern classifications. Such embodiments also include blending the global atmospheric information and the synoptic scale correction factor to produce a data set and blending the data set with atmospheric information from a regional weather model to generate weather fields. Such embodiments further include blending chemical information from a global chemical model and the synoptic scale correction factor to produce a second data set and blending the second data set into a regional chemical model based on the weather fields to forecast the air quality.

Other embodiments include a computer program product and a system.

BRIEF DESCRIPTION OF THE DRAWINGS

The subject matter is particularly pointed out and distinctly claimed in the claims at the conclusion of the specification. The forgoing and other features, and advantages of the embodiments of the present invention described herein are apparent from the following detailed description taken in conjunction with the accompanying drawings, in which:

DETAILED DESCRIPTION

Figure 1:
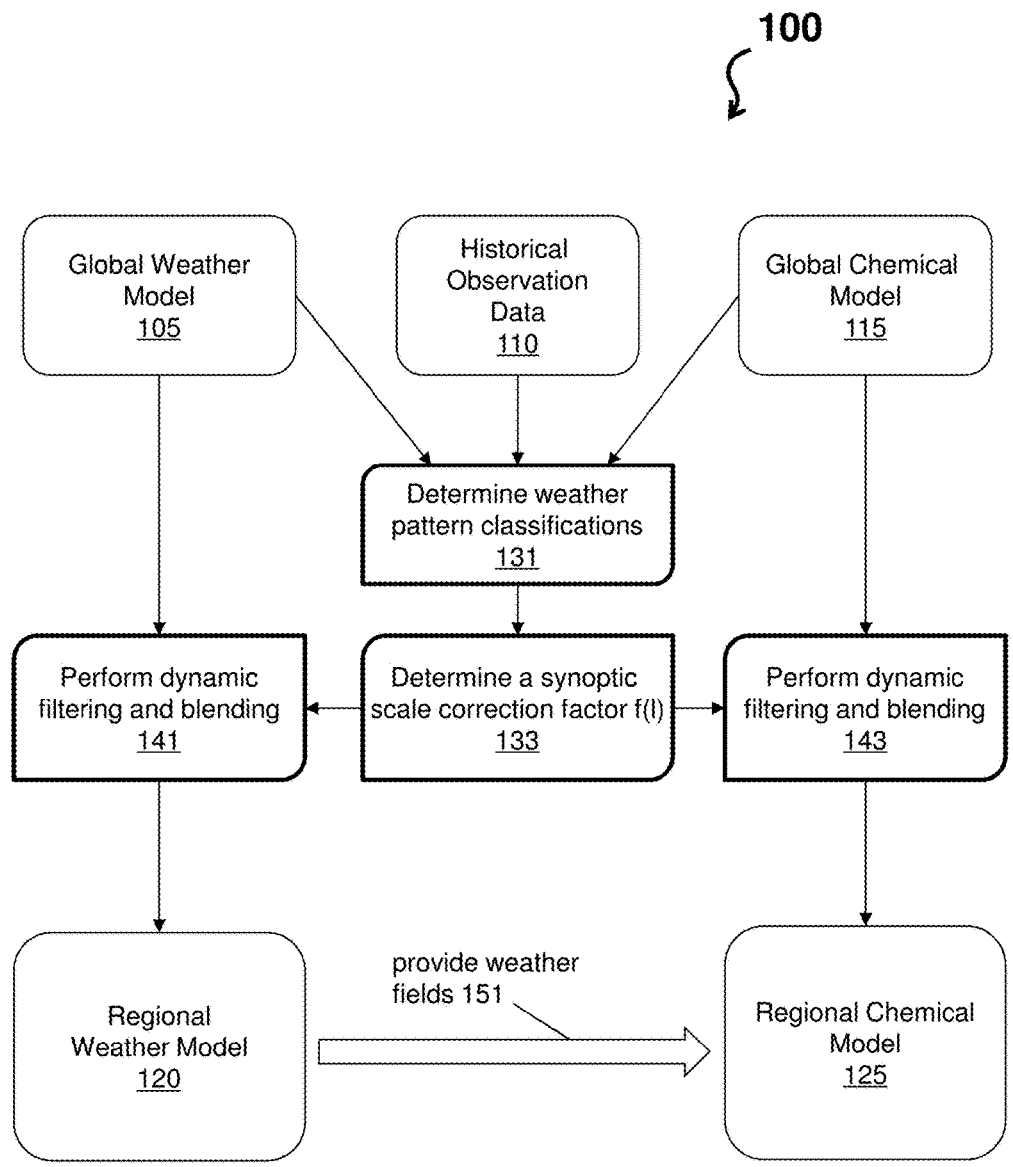
FIG. 1 depicts a block diagram of a forecasting system in accordance with one or more embodiments of the present invention.

There is an increasing interest in the day-to-day air quality conditions to which the public is exposed. One response has been an increasing provision of short-term air pollution forecasts by government authorities. Degradation of visibility in national parks and other pristine areas have also provided motivation for forecasts. Besides issuing alerts and warnings on air quality conditions, some local authorities utilize air quality forecasts in conjunction with intermittent, short-term management strategies, such as free bus/rail fares, additional carpool strategies, burning bans, etc.

Efforts to produce short-term (e.g., 1-3 day) air quality forecasts have relied on a variety of techniques. One technique is based on numerical air quality forecast (NAQF) models. Known NAQF models are understood to have been used to reduce errors that result from an insufficient emission inventory, an inadequate initial background, faulty model parameters, and a small regional domain. For example, known NAQF models may employ operations that attempt to optimize the model parameters (which optimizes the model itself), improve the initial background (e.g., by inserting data assimilation information into the model itself), and/or improve model output statistics (e.g., using linear regression, probability matching, etc.). However, such operations have associated disadvantages. For example, optimizing the model parameters can be costly due to the amount of sensitivity tests required to identify proper optimizations. Improving the initial background can also be costly due to the amount of observations required to create proper data assimilation information. Further, improving the initial background only benefits short term forecasting and does not affect long term forecasting.

Turning now to an overview of aspects of the present invention, some embodiments provide a forecasting system that uses blended global and regional data to improve the accuracy of certain models (e.g., NAQF models). For instance, some embodiments of the present invention blend global (i.e., large-scale) weather forecasts and air quality forecasts with regional (i.e., small-scale) weather forecasts and air quality forecasts in a manner that in improves the effective representation of large-scale features.

In a non-limiting embodiment of the present invention, the forecasting system utilizes historical observation data with respect to large scale (e.g., synoptic scale) and small scale atmospheric information from a global weather model and a regional weather model to determine weather pattern classifications. The weather pattern classifications can be directly utilized by the forecasting system to determine a synoptic scale correction factor f(l). The synoptic scale correction factor f(l) considers the historical filtering accuracy under a specific weather pattern.

Some embodiments of the inventive forecasting system produce one or more blended files (by what is also referred to herein as a "dynamic filtering and blending") that reflect both large and small scale atmospheric information. The blended files can include blended atmospheric information that can be further adjusted by the synoptic scale correction factor f(l). The blended files in accordance with the present invention can also hold more accurate large scale information from the global weather model and more accurate small-scale information from the regional weather model. In some embodiments, the more accurate large scale and small scale information can be balanced dynamically and utilized as initial background for a subsequent forecasting cycle that produces an air quality forecast (e.g., a regional air quality forecast). In this way, for example, embodiments herein can improve the initial background such that short term and long term forecasting benefit.

Figure 2:
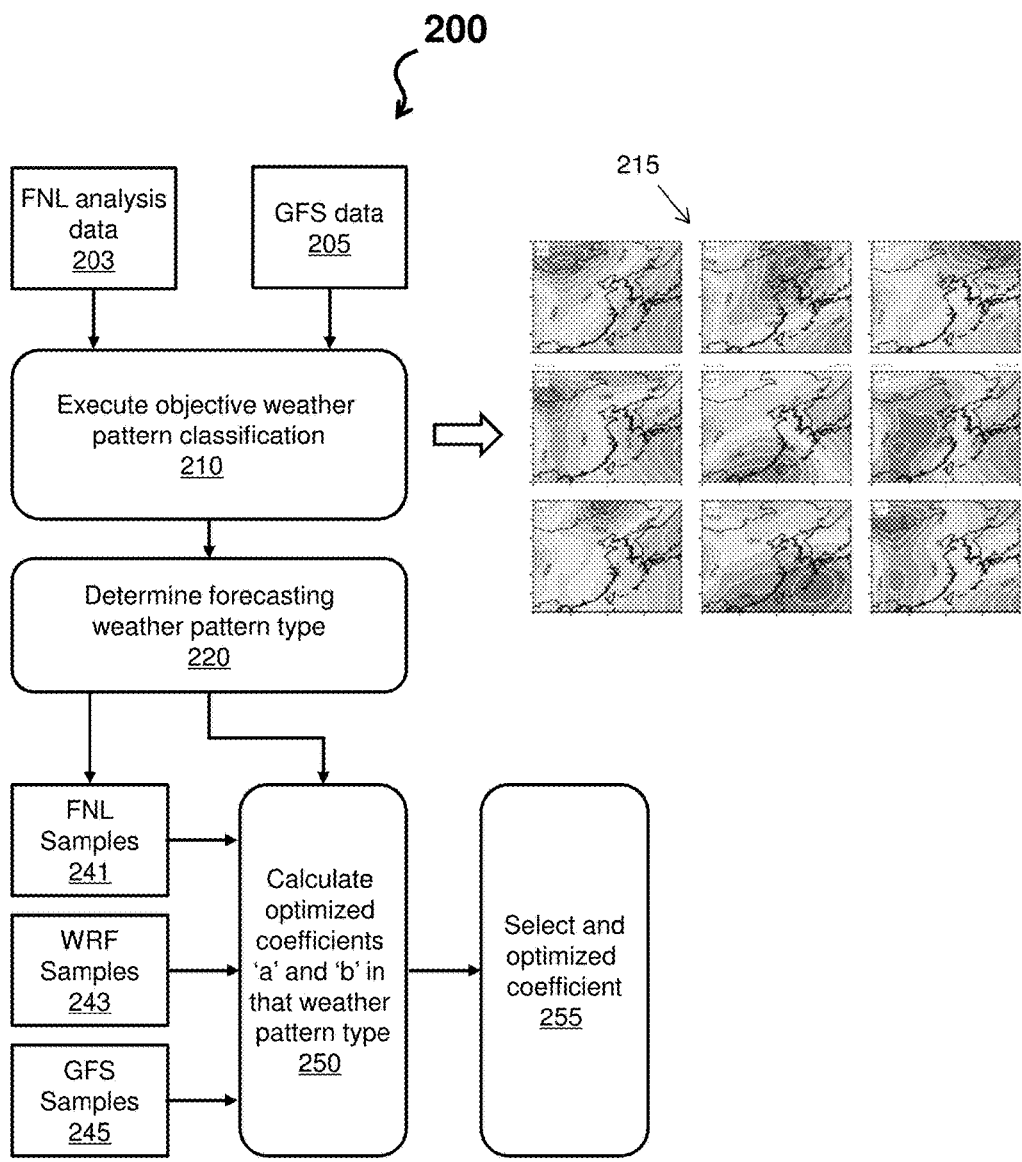
FIG. 2 depicts a forecasting process in accordance with one or more embodiments of the present invention.

Turning now to FIG. 1, a block diagram of a forecasting system 100 is depicted in accordance with one or more embodiments of the present invention. The forecasting system 100 can be an electronic, computer framework that incorporates any number and combination of processing systems (e.g., shown in FIG. 5) and networks utilizing various communication technologies, as known or described herein. As shown, the forecasting system 100 includes a global weather model 105, historical observation data 110, a global chemical model 115, a regional weather model 120, a regional chemical model 125, and a weather pattern classification 120. By way of example only, as will be seen with regard to discussion of the example depicted in FIG. 5, the foregoing can be implemented using hardware and/or software. FIG. 2 depicts a forecasting process. The forecasting process 200 relates to determining a synoptic scale correction factor in accordance with embodiments of the present invention.

A general operation of the forecasting system 100 and the forecasting process 200 will now be described with reference to FIGS. 1 and 2, respectively. Referring now to FIG. 1, the forecasting system 100 utilizes large scale (e.g., synoptic scale) atmospheric information from the global weather model 105, the historical observation data 110, and chemical information from the global chemical model 115 to determine weather pattern classifications 131. Note that a chemical model can be a system for computing air quality indexes with respect to an air pollutant concentration (e.g., obtained from air monitors) over a specified averaging period for a specific region. Air quality index values can be grouped into ranges, each of which being assigned a descriptor, a color code, and/or a standardized public health advisory. Chemical information, in turn, includes the air quality indexes.

Turning now to FIG. 2, final (FNL) analysis data 203 and global forecast system (GFS) data 205 are utilized by the forecasting system 100. FNL analysis data 203 includes data samples with respect to how effective previous GFS data was at forecasting actual weather, such as by providing a gage of historical accuracy for forecast by the GFS. GFS is a non-limiting example of a weather forecast model, such as the model produced by the National Centers for Environmental Prediction (e.g., see GFS at http://www.emc.ncep-.noaa.gov). In block 210, from the FNL analysis data 203 and the GFS data 205 can be used to execute objective weather pattern classifications (e.g., to determine weather pattern classifications 131, FIG. 1). FIG. 2 illustrates a non-limiting example of the generation of objective weather pattern classifications into nine (9) types (e.g., see the nine by nine classification array 215). In this example, weather patterns are classified into nine types using a T-mode component analysis, based on historical observation data 110 of FIG. 1 and/or the FNL analysis data 203 of FIG. 2.

Figure 3:
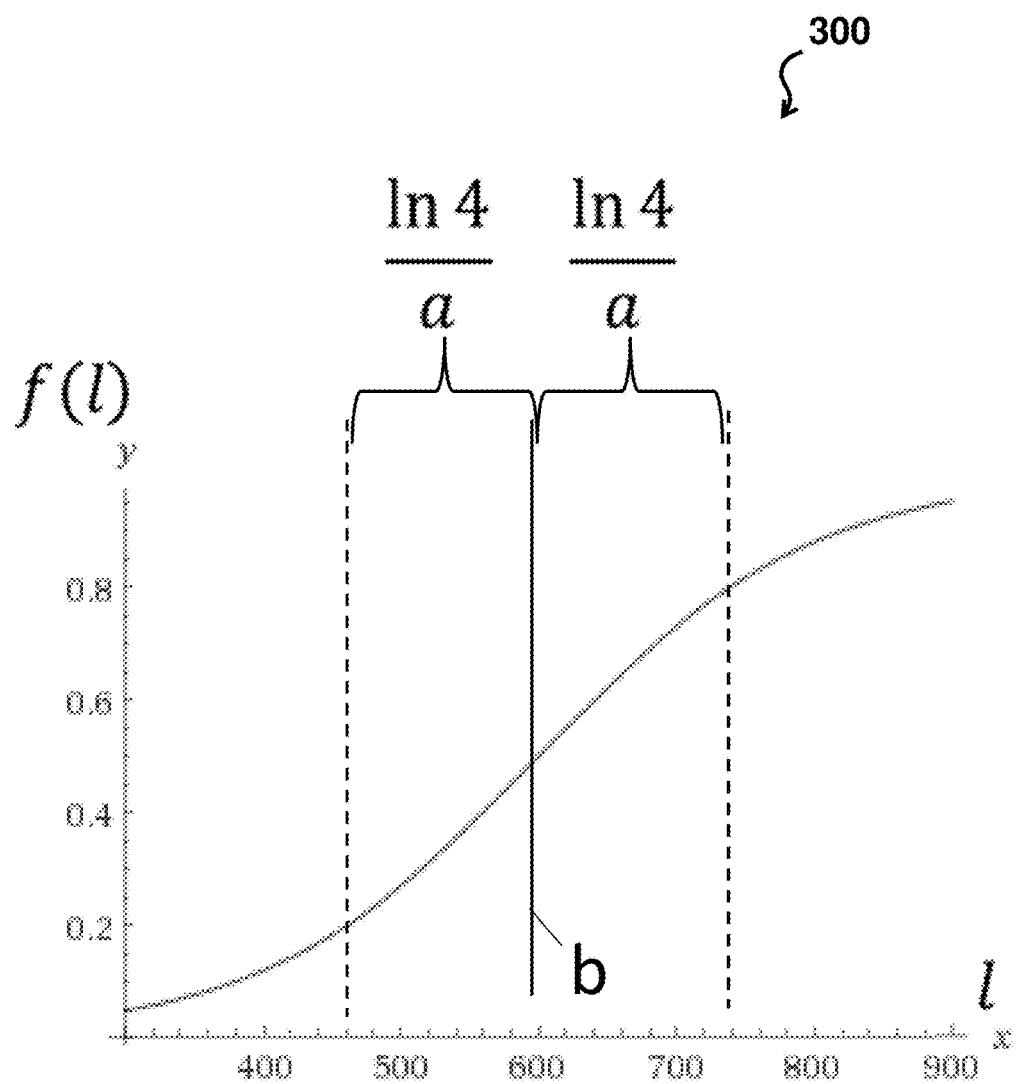
FIG. 3 graphically illustrates an example of optimizing a synoptic scale correction factor in accordance with one or more embodiments of the present invention.

Referring again to FIG. 1, weather pattern classifications 131 can be directly utilized by the forecasting system 100 to determine a synoptic scale correction factor f(l) 133 (as shown in FIG. 3). The synoptic scale correction factor f(l) can be determined by calculating historical performance for the global weather model 105 and the regional chemical model 125 under the same weather pattern. Referring again to FIG. 2, in block 220, a forecasting weather pattern type can be determined based on the objective weather pattern classification (of block 210). The forecasting weather pattern type produced from block 220 is utilized to produce FNL samples 241, weather research and forecasting (WRF) samples 243, and global forecast system (GFS) samples 245, which can be utilized in block 250 to calculate optimized coefficients "a" and "b" based on the forecasting weather pattern type. For example, Table 1 illustrates example values of coefficients "a" and "b" that can be calculated as a root-mean-square error (RMSE) or root-mean-square deviation (RMSD) of a total normalized meteorological variables for coefficients "a" and "b," which are parameters for the synoptic scale correction factor. At block 255, an optimized "a" and "b" for this current weather pattern can be selected. As shown in Table 1, 1.6 is chosen as the optimized value.

TABLE 1

| a | b | | | |
|---|---|---|---|---|
| | 400 km | 600 km | 800 km | 1000 km |
| 0.01 | 2.10 | 1.70 | 2.23 | 2.42 |
| 0.02 | 1.63 | 1.6 | 1.72 | 1.92 |
| 0.03 | 1.69 | 1.65 | 1.75 | 1.74 |
| 0.04 | 1.79 | 1.68 | 1.81 | 1.91 |

Turning to FIG. 3, a graphical illustration of an example of optimizing a synoptic scale correction factor is depicted as a chart 300 in accordance with one or more embodiments of the present invention. The chart 300 shows a plot of the synoptic scale correction factor f(l), which depends on the current weather pattern, as defined by Equation 1, where an x-axis is a distance in kilometers and a y-axis is a synoptic scale.

Equation 1:

$$f(l) = \frac{1}{1 + e^{a(b-l)}}$$

Note that if the "b" coefficient is larger, more of the small scale information from the regional model is used than the large scale information. Alternatively, if the "b" coefficient is smaller, more of the large scale information from the global model is used than the small scale information. The "a" coefficient determines the transformation zone with respect to small scale information and large scale information. After the selecting the optimized value, the synoptic scale correction factor is considered determined by the forecasting system 100.

With the synoptic scale correction factor determined, the large scale information from the global weather model 105 and the global chemical model 115 are blended into the regional weather model 120 and the regional chemical model 125 to improve the accuracy of forecasting. By way of example only, the accuracy of the (regional) air quality forecasting can be improved, e.g., by utilizing longer term (3-10 day) forecasting).

In a non-limiting embodiment of the present invention, the forecasting system 100 performs a dynamic filtering and blending 141 based on the large scale atmospheric information from the global weather model 105 and the synoptic scale correction factor f(l) 133, which considers historical filtering accuracy under a global weather pattern, to produce a first data set (of the global weather model 105 modified by the synoptic scale correction factor). The forecasting system 100 also performs a dynamic filtering and blending 143 based on the chemical information from the global chemical model 115 and the synoptic scale correction factor f(l) 133 to produce a second data set (of the global chemical model 115 modified by the synoptic scale correction factor). Equation 2 is an example of the global weather model 105 in accordance with embodiments of the present invention.

$$G = \Sigma_{l=0}^{\infty} g(l) \varphi_g(l)$$ Equation 2:

Note that a global model weather filed G can be split into components, including a different length scale l, a basis function $\varphi_g(l)$, and a respond function for global field g(l). Equation 3 is an example of the regional weather model 120 in accordance with embodiments of the present invention.

$$R=\Sigma_{l=0}^{\infty}r(l)\varphi_r(l) \qquad \text{Equation 3:}$$

Note that a regional model weather filed R can be also split into components, including a different length scale l, $\varphi_r(l)$ is basis function, and a respond function for regional field r(l). Equation 4 is an example of the blended model that combines the global weather model 105 and the regional weather model 120 in accordance with embodiments of the present invention.

$$B=\Sigma_{l=0}^{\infty}f(l)g(l)\varphi_g(l)+(1-f(l))r(l)\varphi_r(l) \qquad \text{Equation 4:}$$

Note that a first term represents the large-scale information in the global model, and the second term is the small-scale information in the regional model, f(l) is s synoptic scale correction factor that determines how much information from the global model and the regional model are kept in the blended model.

The first data set is provided to the regional weather model 120, while the second data set is provided to the regional chemical model 125. The regional weather model 120 utilizes the small scale atmospheric information in combination with the first data set to provide weather fields 151 to the regional chemical model 125. The regional chemical model 125 utilizes the second data set and the weather field 151 to output a regional air quality forecast.

Figure 4:
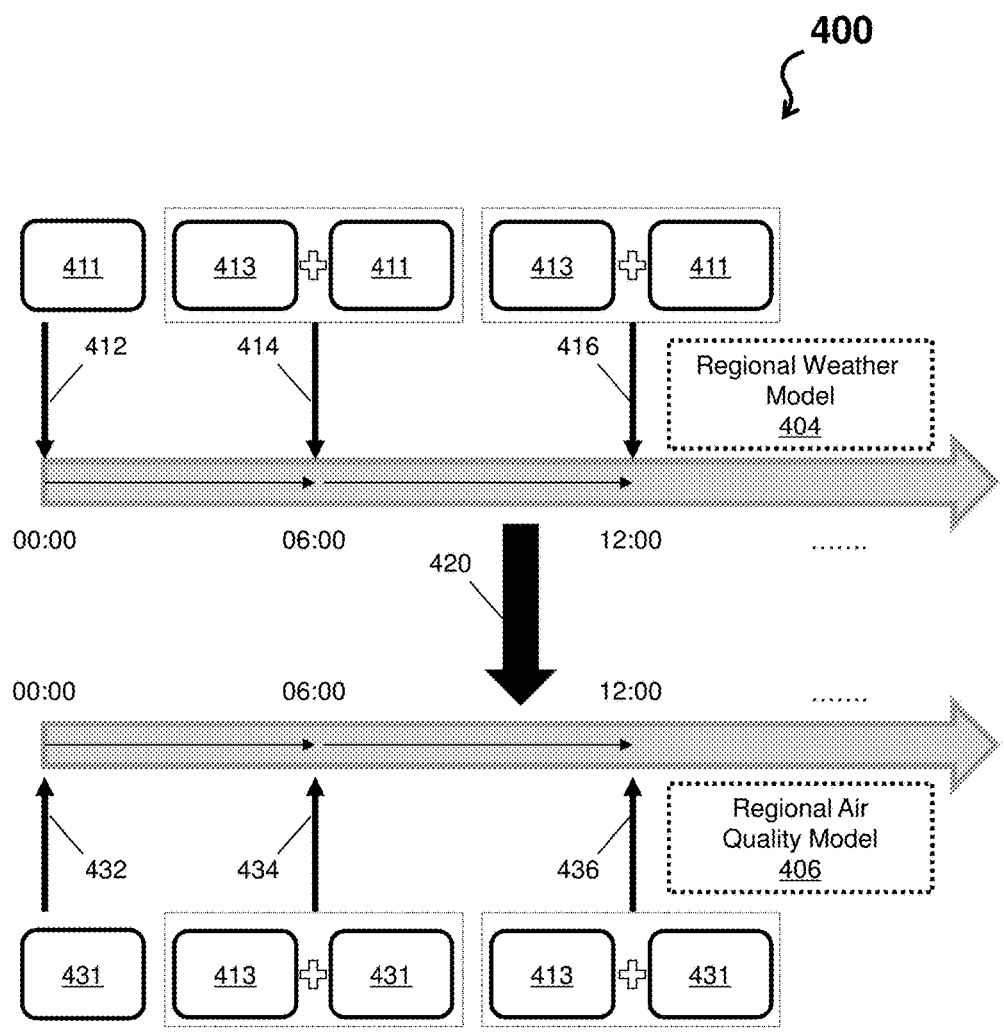
FIG. 4 depicts an operational example of a forecasting system in accordance with one or more embodiments of the present invention.

FIG. 4 depicts an example operation of a forecasting system in accordance with embodiments of the present invention. The example operation is depicted via a diagram 400, which details a blending of multi-scale models of the forecasting system. The blending of multi-scale models (e.g., a regional weather model 404, a regional air quality model 406, a global forecasting system 411, and a global chemical forecast models 431) can be performed with incremental spatial filtering to improve accuracy of the (regional) air quality forecasting, especially for long term forecasting (e.g., 3-10 days).

As shown in FIG. 4 by arrow 412, initial and background conditions for the regional weather model 404 are provided by the global forecasting system 411. As shown by arrows 414 and 416, data of the global forecasting system 411 based on a determined synoptic scale correction factor 413 is blended into the regional weather model 404 at predetermined times (e.g., through incremental spatial filtering). The predetermined times, in a non-limiting embodiment, can be 6 hour intervals. In turn, the forecasting system can hold more accurate large-scale information from the global forecasting system 411 and also maintain small-scale information from the regional weather model 404.

Air quality forecasts of the regional air quality model 406 can be driven by the regional weather blending forecasting (see arrow 420). Further, the air quality forecasts of the regional air quality model 406 can be also blended with the global chemical forecast model 431.

For example, as shown by arrow 432, initial and background conditions for the regional air quality model 406 are provided by the global chemical forecast model 431. As shown by arrows 434 and 436, data of the global chemical forecast model 431 based on the determined synoptic scale correction factor 413 is blended into the regional air quality model 406 at predetermined times (e.g., through incremental spatial filtering). The predetermined times, in a non-limiting embodiment can be intervals of every 6 hours. Thus, by using the dynamical filtering and blending with a determined synoptic scale correction factor, large scale information from global weather and chemical models can be blended into regional model at intervals (e.g., every 6 hours) to improve forecasting accuracy of the regional air quality model 406.

Figure 5:
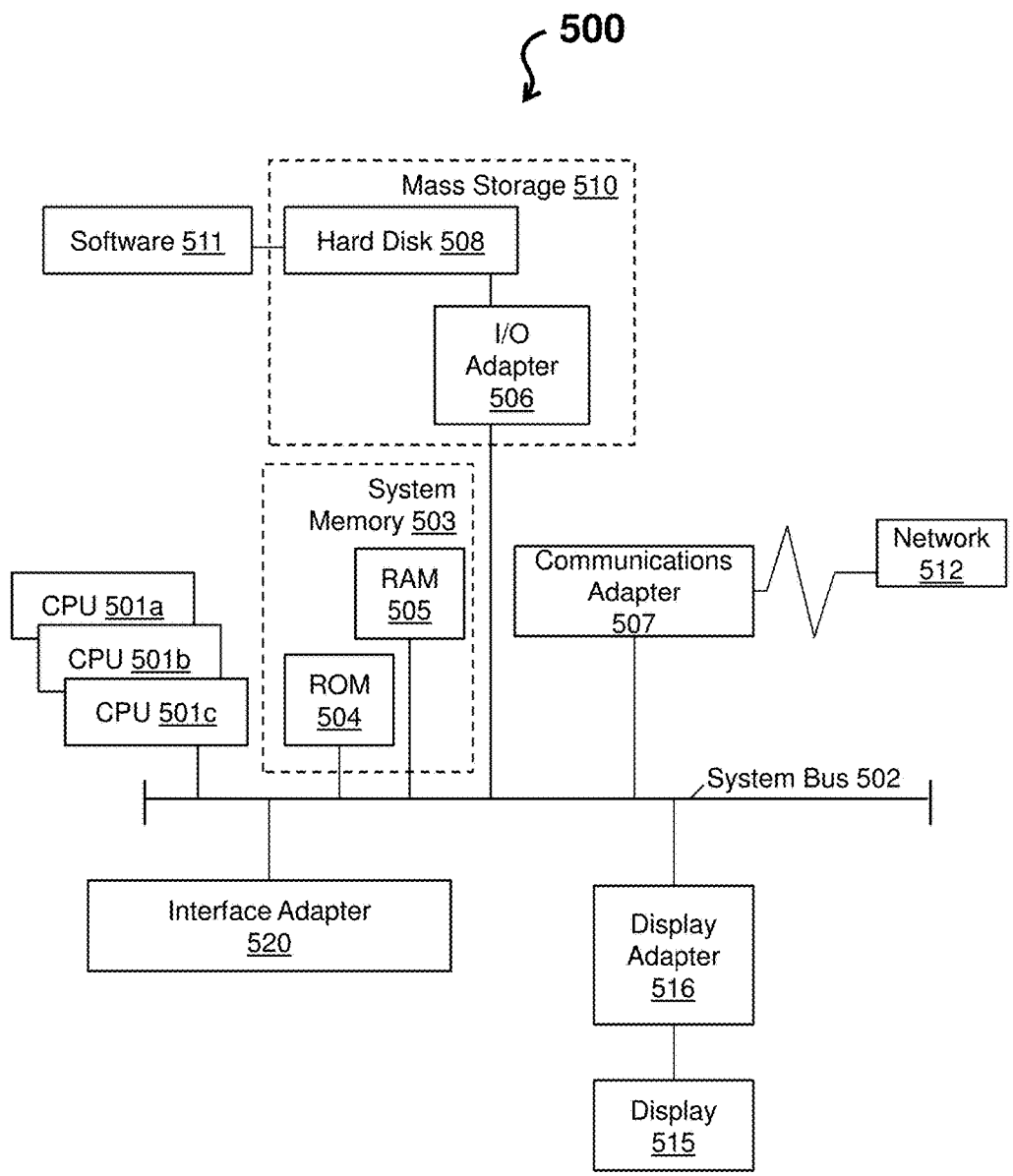
FIG. 5 depicts a forecasting system in accordance with one or more embodiments of the present invention.

FIG. 5 depicts a forecasting system (e.g., system 500) in accordance with one or more embodiments of the present invention. The system 500 has one or more central processing units (CPU(s)) 501a, 501b, 501c, etc. (collectively or generically referred to as processor(s) 501). The processors 501, also referred to as processing circuits, are coupled via a system bus 502 to system memory 503 and various other components. The system memory 503 can include a read only memory (ROM) 504 and a random access memory (RAM) 505. The ROM 504 is coupled to the system bus 502 and may include a basic input/output system (BIOS), which controls certain basic functions of the system 500. The RAM is read-write memory coupled to the system bus 502 for use by the processors 501.

FIG. 5 further depicts an input/output (I/O) adapter 506 and a communications adapter 507 coupled to the system bus 502. The I/O adapter 506 may be a small computer system interface (SCSI) adapter that communicates with a hard disk 508 and/or any other similar component. The I/O adapter 506 and the hard disk 508 are collectively referred to herein as a mass storage 510. A software 511 for execution on the system 500 may be stored in the mass storage 510. The mass storage 510 is an example of a tangible storage medium readable by the processors 501, where the software 511 is stored as instructions for execution by the processors 501 to cause the system 500 to operate, such as is described herein with reference to FIGS. 1-3. Examples of computer program product and the execution of such instruction is discussed herein in more detail. Referring again to FIG. 5, an a communications adapter 507 interconnects the system bus 502 with a network 512, which may be an outside network, enabling the system 500 to communicate with other such systems. A display (e.g., screen, a display monitor) 515 is connected to the system bus 502 by a display adapter 516, which may include a graphics controller to improve the performance of graphics intensive applications and a video controller. In one embodiment, the adapters 506, 507, and 516 may be connected to one or more I/O buses that are connected to the system bus 502 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to the system bus 502 via an interface adapter 520 and the display adapter 516. A keyboard, a mouse, a speaker, etc. can be interconnected to the system bus 502 via the interface adapter 520, which may include, for example, a Super I/O chip integrating multiple device adapters into a single integrated circuit.

Thus, as configured in FIG. 5, the system 500 includes processing capability in the form of the processors 501, and, storage capability including the system memory 503 and the mass storage 510, input means such as the keyboard and the mouse, and output capability including the speaker and the display 515. In one embodiment, a portion of the system memory 503 and the mass storage 510 collectively store an operating system, such as the z/OS or AIX operating system from IBM Corporation, to coordinate the functions of the various components shown in FIG. 5.

Technical effects and benefits of the forecasting system herein include overcoming the shortcomings of a regional domain model being limited to a regional domain by performing a dynamic filtering and blending of a global domain model and the regional domain model with a synoptic scale correction faction. Thus, embodiments of the present invention described herein are necessarily rooted in a processor of the forecasting system to perform proactive operations to overcome problems specifically arising in the realm of air quality forecasting The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the present invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method of forecasting air quality, the method comprising:
   determining, by a processor, weather pattern classifications based on global atmospheric information from a global weather model;
   determining, by the processor, a synoptic scale correction factor in response to determining the weather pattern classifications;
   blending, by the processor, the global atmospheric information and the synoptic scale correction factor to produce a data set;
   blending, by the processor, the data set with regional atmospheric information from a regional weather model to generate weather fields;
   blending, by the processor, chemical information from a global chemical model and the synoptic scale correction factor to produce a second data set; and
   blending, by the processor, the second data set into a regional chemical model based on the weather fields to forecast the air quality.

2. The computer-implemented method of claim 1, wherein the weather pattern classifications are based on the global atmospheric information, historical observation data, and chemical information from the global chemical model.

3. The computer-implemented method of claim 1 further comprising determining the weather pattern classifications based on the chemical information from the global chemical model and the global atmospheric information.

4. The computer-implemented method of claim 1, wherein the synoptic scale correction factor is determined by calculating historical performance for the global weather model and the regional chemical model under a first weather pattern.

5. The computer-implemented method of claim 1, wherein the synoptic scale correction factor is determined from an optimized set of coefficients.

6. The computer-implemented method of claim 5, wherein the optimized set of coefficients is calculated from normalized meteorological variables.

7. The computer-implemented method of claim 1, wherein the weather patterns are classified a T-mode component analysis.

8. A computer program product for forecasting air quality, the computer program product comprising a computer readable storage medium having program instructions embodied therewith, the program instructions executable by a processor to cause the processor to:
   determine weather pattern classifications based on global atmospheric information from a global weather model;
   determine a synoptic scale correction factor in response to the determination of the weather pattern classifications;
   blend the global atmospheric information and the synoptic scale correction factor to produce a data set;
   blend the data set with regional atmospheric information from a regional weather model to generate weather fields;
   blend chemical information from a global chemical model and the synoptic scale correction factor to produce a second data set; and
   blend the second data set into a regional chemical model based on the weather fields to forecast the air quality.

9. The computer program product of claim 8, wherein the weather pattern classifications are based on the global atmospheric information, historical observation data, and the chemical information from the global chemical model.

10. The computer program product of claim 8, wherein the program instructions are further executable by the processor to cause the processor to:
    determine the weather pattern classifications based on the chemical information from the global chemical model and the global atmospheric information.

11. The computer program product of claim 8, wherein the synoptic scale correction factor is determined by calculating historical performance for the global weather model and the regional chemical model under a first weather pattern.

12. The computer program product of claim 8, wherein the synoptic scale correction factor is determined from an optimized set of coefficients.

13. The computer program product of claim 12, wherein the optimized set of coefficients is calculated from normalized meteorological variables.

14. The computer program product of claim 8, wherein the weather patterns are classified a T-mode component analysis.

15. A system for forecasting air quality, comprising a processor and a memory storing program instructions thereon, the program instructions executable by a processor to cause the system to:
    determine weather pattern classifications based on global atmospheric information from a global weather model;
    determine a synoptic scale correction factor in response to the determination of the weather pattern classifications;
    blend the global atmospheric information and the synoptic scale correction factor to produce a data set;
    blend the data set with regional atmospheric information from a regional weather model to generate weather fields;
    blend chemical information from a global chemical model and the synoptic scale correction factor to produce a second data set; and
    blend the second data set into a regional chemical model based on the weather fields to forecast the air quality.

16. The system of claim 15, wherein the weather pattern classifications are based on the global atmospheric information, historical observation data, and the chemical information from the global chemical model.

17. The system of claim 15, wherein the program instructions are further executable by the processor to cause the system to:
   determine the weather pattern classifications based on the chemical information from the global chemical model and the global atmospheric information.

18. The system of claim 15, wherein the synoptic scale correction factor is determined by calculating historical performance for the global weather model and the regional chemical model under a first weather pattern.

19. The system of claim 15, wherein the synoptic scale correction factor is determined from an optimized set of coefficients.

20. The system of claim 19, wherein the optimized set of coefficients is calculated from normalized meteorological variables.

\* \* \* \* \*